(12) United States Patent
Wang et al.

(10) Patent No.: US 10,087,466 B2
(45) Date of Patent: Oct. 2, 2018

(54) METHOD OF SYNTHESIZING BIOGENIC ELEMENTAL SELENIUM NANOSTRUCTURE USING ENTEROBACTER CLOACAE AND APPLICATION THEREOF

(71) Applicant: Zhejiang University, Hangzhou, Zhejiang Province (CN)

(72) Inventors: Yizhen Wang, Hangzhou (CN); Deguang Song, Hangzhou (CN); Zeqing Lu, Hangzhou (CN); Fengqin Wang, Hangzhou (CN); Yuanzhi Cheng, Hangzhou (CN); Xiaoxiao Li, Hangzhou (CN)

(73) Assignee: Zhejiang University, Hangzhou, Zhejiang Province (CN)

( * ) Notice: Subject to any disclaimer, the term of this patent is extended or adjusted under 35 U.S.C. 154(b) by 0 days.

(21) Appl. No.: 15/397,711

(22) Filed: Jan. 3, 2017

(65) Prior Publication Data

US 2017/0191083 A1 Jul. 6, 2017

(30) Foreign Application Priority Data

Jan. 4, 2016 (CN) .......................... 2016 1 0000452

(51) Int. Cl.
| | | |
|---|---|---|
| *C12P 3/00* | (2006.01) | |
| *C01B 19/02* | (2006.01) | |
| *A23L 33/16* | (2016.01) | |

(52) U.S. Cl.
CPC ................. *C12P 3/00* (2013.01); *A23L 33/16* (2016.08); *C01B 19/02* (2013.01)

(58) Field of Classification Search
CPC .................................. C12P 3/00; C01B 19/02
See application file for complete search history.

(56) References Cited

FOREIGN PATENT DOCUMENTS

CN 10475916 * 7/2009

OTHER PUBLICATIONS

Xu et al "Preparation, characterization and immunomodulatory activity of selenium-enriched exopolysaccharide produced by bacterium Enterobacter cloacae Z0206". Bioresource Technology. 2009, 100, pp. 2095-2097.*
Jain, Rohan. "Biogenic nanoparticles of elemental selenium synthesis, characterization and relevance in wastewater treatment". PhD thesis, Universite Paris-Est, Unesco-Institute for Water Education, Dec. 2014, pp. 1-262.*
Watts et al. FEMS Microbiology Letters, 2003, 228, pp. 273-279.*

* cited by examiner

*Primary Examiner* — Vera Afremova
(74) *Attorney, Agent, or Firm* — Shuang Chang; PSK Intellectual Property Group, LLC

(57) ABSTRACT

A method of synthesizing biogenic elemental selenium nanostructure using *Enterobacter cloacae* and its application. The method uses *E. cloacae* Z0206 to reduce selenite to zero valence selenium and forms nano-sized elemental selenium particles, including steps of inoculating activated *E. cloacae* Z0206 to fermentation broth, adding sodium selenite solution, shaking and incubating, collecting the fermentation broth and separating the elemental selenium nanoparticles.

2 Claims, 4 Drawing Sheets

METHOD OF SYNTHESIZING BIOGENIC ELEMENTAL SELENIUM NANOSTRUCTURE USING ENTEROBACTER CLOACAE AND APPLICATION THEREOF

CROSS-REFERENCE TO RELATED APPLICATIONS

This non-provisional application claims priority to and benefit of, under 35 U.S.C. § 119(a), Patent Application No. 201610000452.9 filed in P. R. China on Jan. 4, 2016, the entire content of which is hereby incorporated by reference.

FIELD OF THE INVENTION

The present invention relates to the field of microbial application, nanostructure elemental selenium synthesis and biological feed additives, more particularly to a method for synthesizing biogenic elemental Selenium nanostructures using bacteria and its application in pig production.

BACKGROUND OF THE INVENTION

Selenium is one of the essential trace elements for human and animals, which is fundamental to health. Selenium-deficiency in human affects nervous system, reproductive system, immune system and cardiovascular system. Selenium-deficiency in animals often results in dysfunction in reproductive system, decrease of reproductive performance, growth inhibition, and muscle lesions (such as white muscle disease, cardiomyopathy and skeletal muscle myopathy), etc. Human and animals maintain selenium requirements by obtaining selenium from soil through food chain. People with selenium intake deficiency are facing health risks. Currently recognized as the safest and most efficient selenium supplement form is Selenomethionine (SeMet). Comparing with SeMet, elemental selenium is regarded as biological inert with neither activity nor toxicity. However, recent years, research has indicated that comparing with SeMet, nano-sized elemental selenium particles possess similar biological activity and even lower toxicity.

Selenium nanoparticle biogenesis mostly uses ascorbic acid, sodium thiosulfate, sodium sulphite or hydrazine to reduce selenium dioxide, selenite or selenate to synthesize selenium nanostructure. Chemically synthesized selenium nanostructures require surfactant or stabilizer (proteins or polysaccharides, etc.) to maintain stability, otherwise, they transform easily into black, toxic elemental selenium. In addition, the process of selenium nanostructure synthesis introduces toxic materials, which pollutes the environment. It has been proven that some bacteria could reduce selenium oxyanions to zero-valence selenium and form nanostructure particles, which are sphere shaped, uniform sized, and more stable, comparing with chemically synthesized selenium nanostructures. Moreover, bacterial fermentation isn't usually influenced by temperature and season. Bacterial fermentation for biogenic selenium nanostructure synthesis is also characterized by strong production capacity and short production cycle. Therefore, using bacteria to synthesize biogenic elemental selenium nanostructure may be a safe and efficient way for the future.

The present invention relates to a method of using E. cloacae to synthesize biogenic elemental selenium nanostructures.

SUMMARY OF THE INVENTION

Therefore, the objective of the present invention is to provide a method of using E. cloacae to synthesize biogenic elemental selenium nanostructures and to overcome drawbacks of the existing technologies.

In one aspect, the present invention provides a method of using E. cloacae to synthesize biogenic elemental selenium nanostructures using selenite as the starting material and E. cloacae as the fermentative bacteria.

Preferably, the method includes the following steps:
inoculate activated E. cloacae Z0206 cells to fermentation broth, add sodium selenite solution into the fermentation broth;
shake and incubate;
collect the fermentation broth and centrifuge, collect the supernatant after the centrifugation, centrifuge the supernatant once again, re-suspend the sediment with double distilled water, ultrasonicate the suspension, add hexane, mix and stratify by standing. The biogenic elemental selenium nanostructures should present in the lower red aqueous phase. The parameters of the first centrifugation are 4° C., 5,000×g, 15 min. The parameters of the second centrifugation are 4° C., 25,000×g, 15 min. The parameters of the ultrasonication are 25 W, 5 s on/5 s off, 15 min. The volume of hexane is half of the volume of the suspension;

The E. cloacae strain Z0206 utilized here is deposited in China General Microbiological Culture Collection Center (CGMCC) on Dec. 3, 2007 with a CGMCC depository No. 2279.

Preferably, in the first step, the broth composition contains sucrose (25 g·L$^{-1}$), yeast extraction (5 g·L$^{-1}$), tryptone (5 g·L$^{-1}$), $K_2HPO_4·3H_2O$ (2.62 g·L$^{-1}$), $KH_2PO_4$ (1 g·L$^{-1}$) and $MgSO_4$ (0.5 g·L$^{-1}$); the initial pH value is 7.5.

Preferably, in the first step, the final concentration of sodium selenite in the broth is 10 mM.

Preferably, in the first step, the temperature, rotation speed and incubation time are 32° C., 250 rpm and 144 hours, respectively.

An application of the biogenic elemental selenium nanostructures synthesized using the method of the present invention, where the biogenic elemental selenium nanostructures replace the use of sodium selenite in pig feed.

The present invention further optimizes all the parameters of the synthesis and separation process, overcomes the potential defect of biogenic elemental selenium nanostructures and the uncertainty of production. The present invention is easy to produce and to be applied at industrial scale.

The biogenic elemental selenium nanostructures and biogenic elemental selenium nanostructure-polysaccharides complex could replace sodium selenite in pig feed, which could improve antioxidative capacity and immunity, and promote the growth of pig.

DETAILED DESCRIPTION OF THE INVENTION

Embodiment 1: Effect of Different Concentrations of Sodium Selenite on *E. Cloacae* Z0206 Growth and Selenite Reduction Rate 1. Broth Preparation LB broth: 10 g NaCl, 10 g tryptone and 5 g yeast extraction were dissolved in 1 L double distilled water, sterilized at 100 kPa, 121° C. for 20 min.

LB agar plate: 10 g NaCl, 10 g tryptone, 5 g yeast extraction and 15 g agar were dissolved in 1 L double distilled water, sterilized at 100 kPa, 121° C. for 20 min.

Fermentation broth: 25 g sucrose, 5 g yeast extraction, 5 g tryptone, 2.62 g $K_2HPO_4 \cdot 3H_2O$, 1 g $KH_2PO_4$ and 0.5 g $MgSO_4$ were dissolved in 1 L double distilled water, adjusted the initial pH value to 7.5, sterilized at 67 kPa, 115° C. for 30 min.

2. Bacteria Activation

Bacterial stock from −80° C. was thawed, a loop of bacteria was taken and streaked on LB agar plate, cultivated at 32° C. for 24 h.

A single colony was picked and inoculated into LB broth, cultivated at 32° C., 250 rpm for 18 h.

3. Inoculation and Fermentation

Cell density was adjusted to $OD_{600}$=0.5 with PBS, 1% of the bacteria cells were inoculated to fermentation broth containing 0 mM, 0.5 mM, 1 mM, 5 mM, 10 mM and 15 mM sodium selenite, respectively. Each concentration gradient was repeated for three times. Cells were fermented at 32° C., 250 rpm, and the fermentation broth was collected at 4 h, 8 h, 12 h, 16 h, 20 h, 24 h, 36 h, 48 h, 72 h and 96 h after inoculation for detecting cell protein content in order to characterize bacterial cell density; fermentation broth was also collected at 0 h, 12 h, 24 h, 36 h, 48 h, 72 h, 96 h, 120 h, 144 h and 168 h after inoculation for detecting sodium selenite residue.

4. Results

Figure 1:
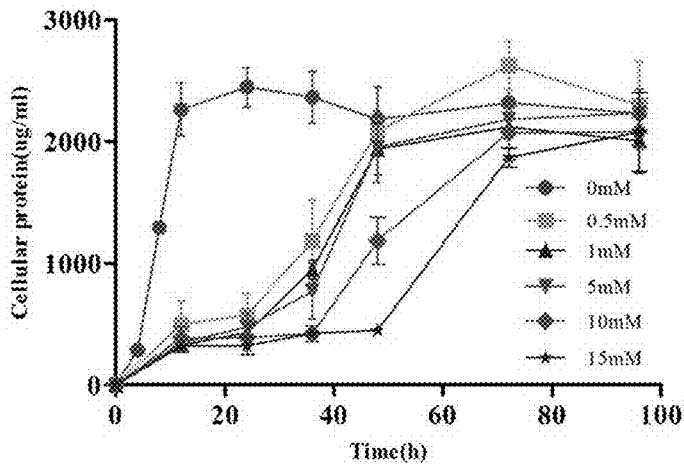
FIG. 1: Effect of different concentrations of sodium selenite on the growth of E. cloacae Z0206.

As shown in FIG. 1, growth of control group *E. cloacae* Z0206 reached stationary phase at 12 h, while addition of sodium selenite significantly decreased the growth rate of *E. cloacae* Z0206, and the inhibition increased with the increase of sodium selenite concentration.

Figure 2:
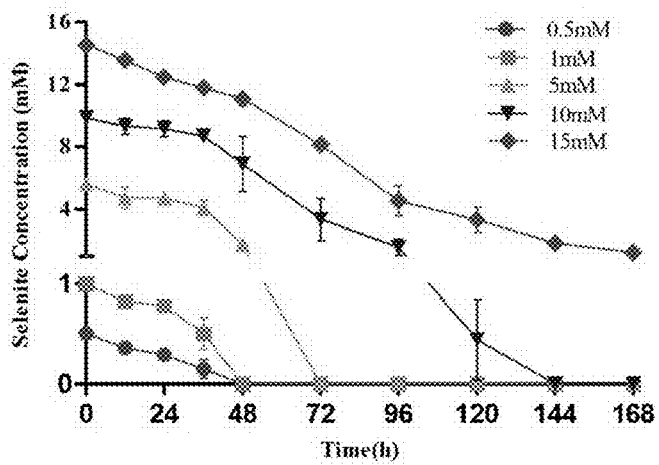
FIG. 2: Changes of sodium selenite residue in E. cloacae Z0206 fermentation broth at different concentrations of sodium selenite.
Figure 3:
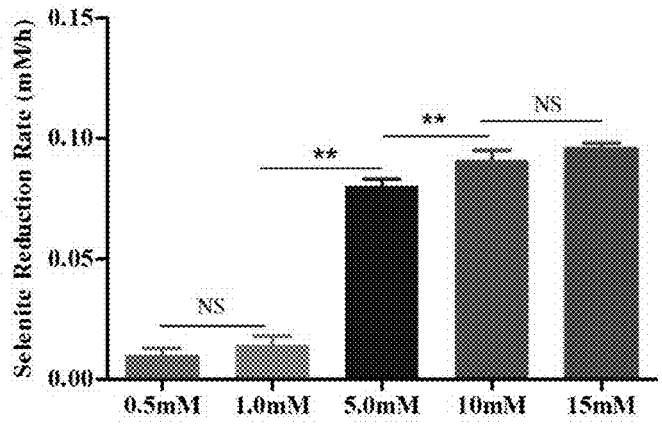
FIG. 3: Average consumption rate of sodium selenite by E. cloacae Z0206 at different concentrations of sodium selenite.

FIGS. 2-3 show the sodium selenite reduction rates of *E. cloacae* Z0206 at different concentrations of sodium selenite. *E. cloacae* Z0206 started to consume sodium selenite at the beginning of cultivation. Sodium selenite of groups of 0.5 mM, 1 mM, 5 mM and 10 mM was completely consumed at 48 h, 48 h, 72 h and 144 h after inoculation, respectively. Sodium selenite reduction rate of the 15 mM group was only 91.35%±1.40% at the end of point of monitoring (168 h).

Embodiment 2: Synthesis of Biogenic Elemental Selenium Nanostructure Using *E. Cloacae* Z0206 and Sodium Selenite Activated *E. cloacae* Z0206 cell density was adjusted to $OD_{600}$=0.5 with PBS, 1% of the bacteria cells were inoculated to the fermentation broth, sodium selenite solution was added to a final concentration of 10 mM, cultivated at 32° C., 250 rpm for 144 h.

Embodiment 3: Electronic Microscope Analysis and Energy-Dispersive X-Ray Spectroscopy Analysis of Bacteria Cells and Biogenic Elemental Selenium Nanostructures 1 mL fermentation broth was collected according to the steps of Embodiment 2. After centrifugation, the sediment was washed three times with PBS and fixed with 2.5% glutaraldehyde solution for 12 h. The sediment was then washed again three times with PBS, followed by 1% osmic acid fixation, ethanol gradient dehydration, isoamyl acetate treatment, critical point drying and gold plating. Samples were analysed with environmental scanning electron microscope (ESEM) and energy-dispersive X-ray spectroscopy (EDX) analysis.

Figure 4:
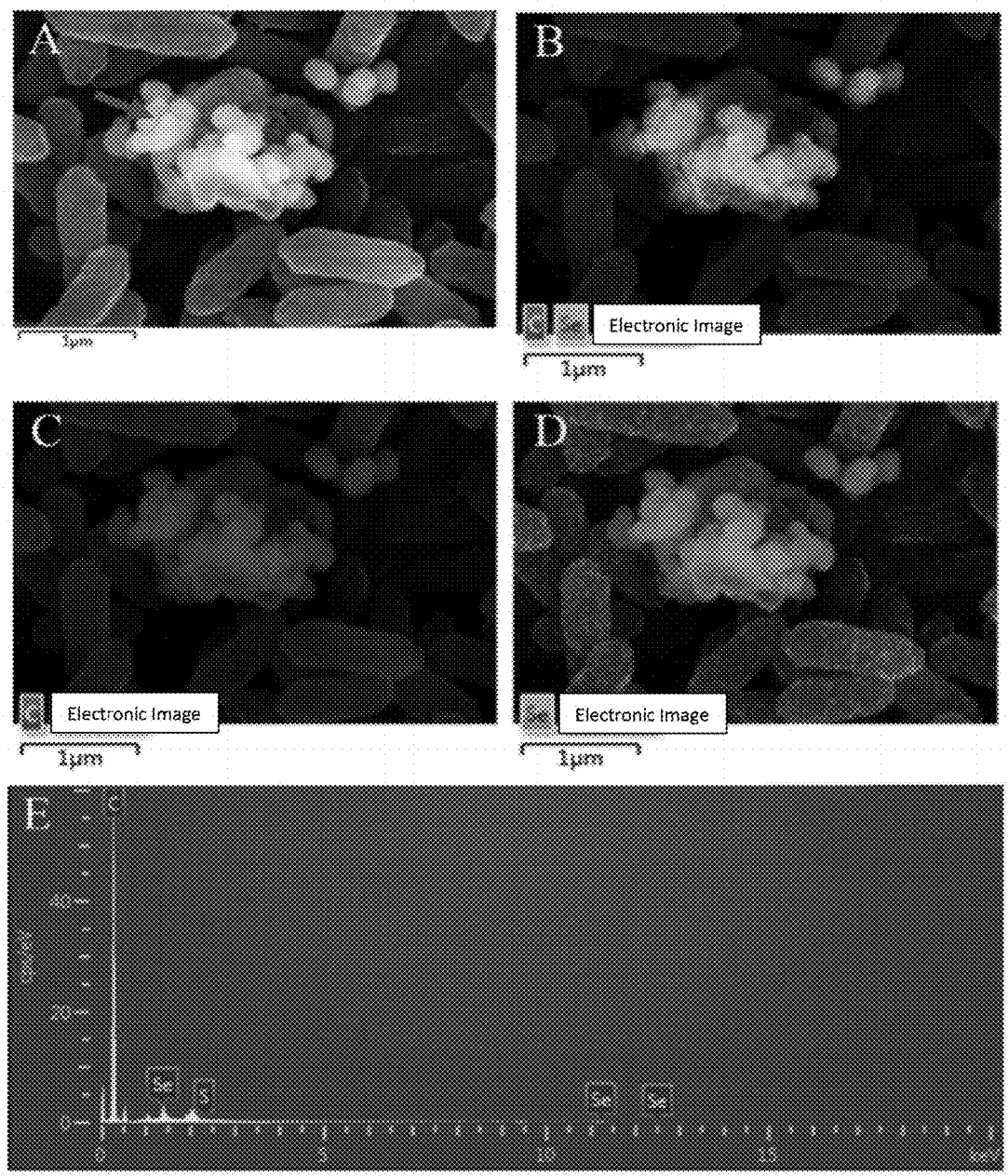
FIG. 4: Environmental scanning electronic microscope (ESEM) analysis and energy dispersive x-ray spectrum (EDX) analysis of E. cloacae Z0206 cells and biogenic elemental selenium nanostructures. (A) ESEM images; (B) Merge of the element distribution maps of carbon and selenium; (C) Element distribution map of carbon; (D) Element distribution map of selenium; (E) EDX analysis.

As shown in FIG. 4, *E. cloacae* Z0206 reduced sodium selenite to regular spherical nanoparticles (FIG. 4A, indicated by arrow). These particles were monodisperse with sizes range between 100 nm to 200 nm. The extracellular nanoparticles were identified as elemental nano-selenium by EDX analysis, and these particles may be capped with a layer of carbon-containing organic matter.

1 mL fermentation broth was collected according to the steps of Embodiment 2. After centrifugation, the sediment was washed three times with PBS and fixed with 2.5% glutaraldehyde solution for 12 h. The sediment was then washed again three times with PBS, followed by agarose pre-embedding. The samples were treated with 1% osmic acid, ethanol gradient and embedding agent, followed by heating at 70° C., slicing and dying. The samples were analyzed with transmission electron microscopy (TEM) and EDX.

Figure 5:
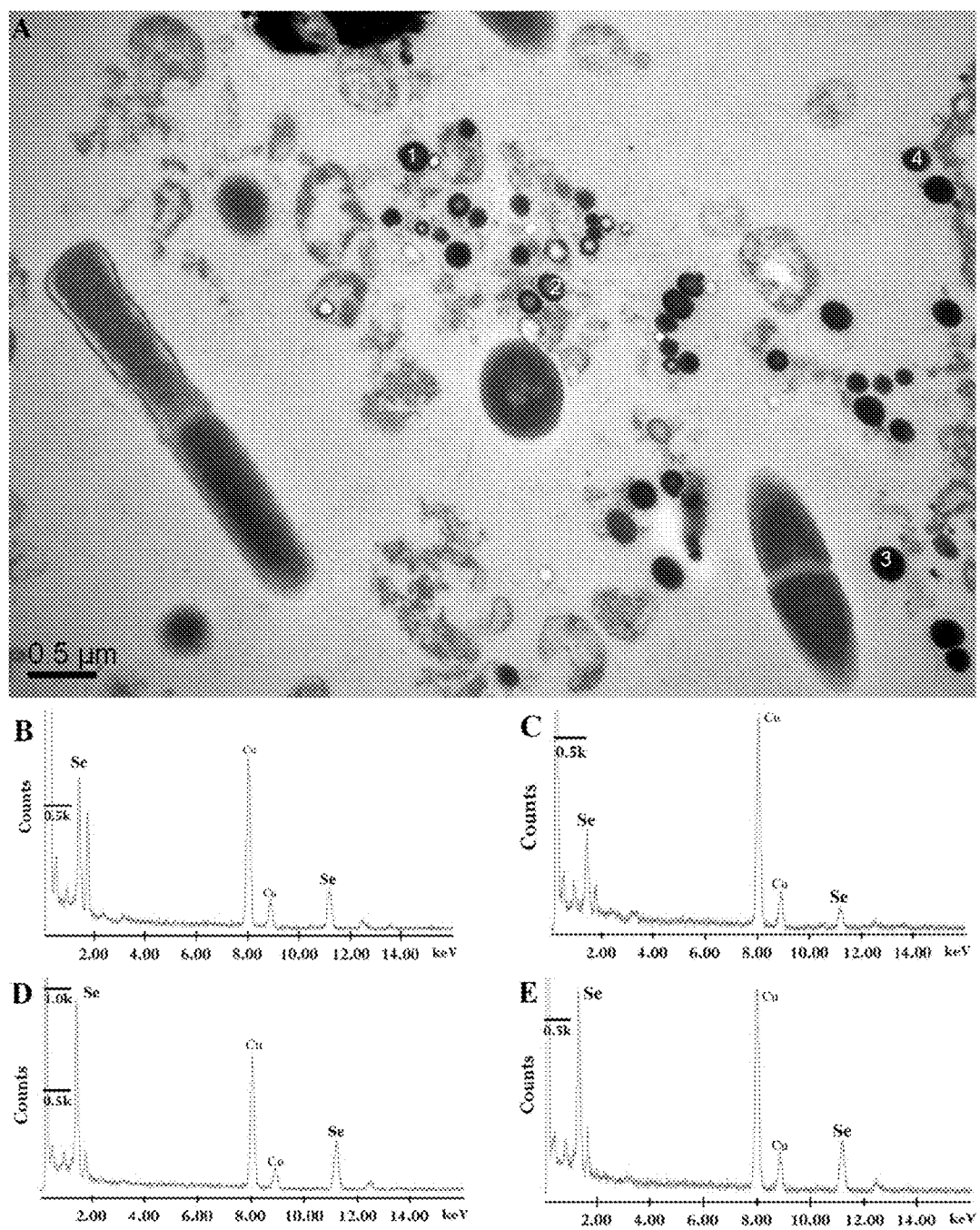
FIG. 5: Transmission electronic microscope (TEM) analysis and EDX analysis of *E. cloacae* Z0206 cell and biogenic elemental selenium nanostructures. (A) TEM images; (B) EDX analysis of particle 1; (C) EDX analysis of particle 2; (D) EDX analysis of particle 3; (E) EDX analysis of particle 4.

As shown in FIG. 5, TEM analysis confirmed that *E. cloacae* Z0206 reduced sodium selenite to extracellularly located spherical nanoparticles, with sizes ranging between 100 nm to 200 nm. EDX analysis confirmed that these particles were elemental nano-selenium.

Embodiment 4: Biogenic Elemental Selenium Nanostructure Separation, Purification and Characterization 1. Fermentation broth according to Embodiment 2 was collected, centrifuged at 5,000×g for 15 min, the sediment was discarded.

2. The supernatant was centrifuged at 4° C., 25,000×g for 15 min, the supernatant was discarded and the sediment was collected.

3. The sediment was re-suspended with double distilled water, ultrasonicated at 25 W, 5 s on/5 s off for 15 min.

4. Hexane (half volume of above mentioned suspension) was added, vortexed and mixed, and let stand to stratification. The biogenic elemental selenium nanoparticles were present in the lower aqueous phase and the lower aqueous phase was collected, which was a biogenic elemental selenium nanoparticle suspension.

5. A drop of the biogenic elemental selenium nanoparticle suspension was added to a copper net, dried with paper filter, and analysed with TEM;

6. A drop of the biogenic elemental selenium nanoparticle suspension was analysed with nano-sizer to measure particle size.

Figure 6:
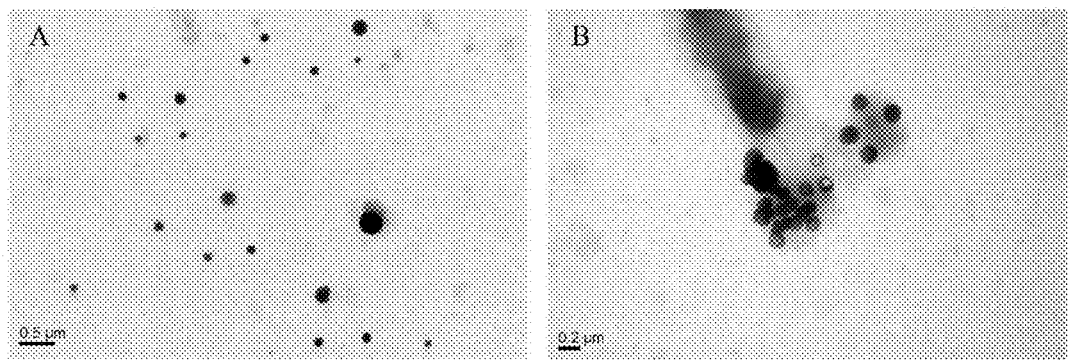
FIG. 6: TEM images of separated biogenic elemental selenium nanostructures.
Figure 7:
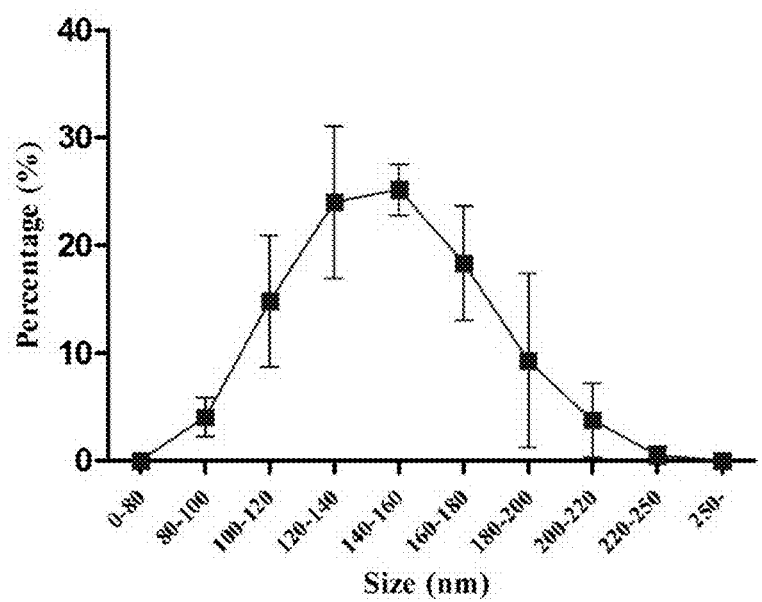
FIG. 7: Size analysis of separated biogenic elemental selenium nanostructures.

As shown in FIG. 6, TEM analysis showed that the biogenic elemental selenium nanoparticles were monodisperse, regular spheres, with sizes range between 100 nm to 200 nm. Particle size analysis (FIG. 7) showed that the biogenic elemental selenium nanoparticles ranged between 80 nm to 250 nm, with the average size of 144.10±1.14 nm.

Embodiment 5: Biogenic Elemental Selenium Nanostructure-Polysaccharides Complex Separation 1. The fermentation broth according to Embodiment 2 was collected by centrifuging at 5,000×g for 15 min. The supernatant was collected.

2. Pre-cooled ethanol (3-fold volumes of the supernatant) was added to the supernatant, centrifuged at 5,000×g for 15 min. The obtained sediment was the biogenic elemental selenium nanostructure-polysaccharides complex.

Embodiment 6: Application of Biogenic Elemental Selenium Nanostructure in Pig 1. Experiment Design Ninety 28-day-old weaned pigs were randomly divided into three groups, with three replicates per group, and ten pigs per replicate. The control group was fed with basic diet, the experimental group 1 was fed with basic diet supplied with 0.3 mg/kg $Na_2SeO_3$, and the experimental group 2 was fed with basic diet supplied with 0.14 mg/kg biogenic elemental selenium nanostructure. Diet composition and nutrient levels were shown in Table 1.

TABLE 1

Basic diet and nutrient levels

| Composition (%) | | Nutrient levels | |
|---|---|---|---|
| Corn | 59.3 | Digestible energy (MJ/kg) | 14.43 |
| Dehulled soybean meal | 8.0 | Crude protein (%) | 19.50 |
| Extruded soybean | 6.0 | Ca (%) | 0.79 |
| Fermented soybean meal | 7.0 | Total P (%) | 0.60 |
| Whey powder | 6.0 | Lys (%) | 1.50 |
| Plasma protein | 2.5 | Thr (%) | 0.98 |
| Fish meal | 3.0 | Met (%) | 0.52 |
| Soybean oil | 2.5 | Trp (%) | 0.18 |
| monocalcium phosphate | 0.9 | Se (%) | 0.10 |
| Stone powder | 0.8 | | |
| Premix | 4.0 | | |

2. Feeding and Management

During the experimental process, pigs were kept in pigpen with slatted floor, automatic feeder and duckbill type drinker. Anthelmintic work and vaccination were performed according to the farm management.

Growth Measurement

Pig body weight was measured at 28-day-old and 67-day-old, respectively. Food consumption data was collected. Average daily feed intake, average daily weight gain and feed/gain ratio was calculated.

Sample Collection

After 12 h fasting, pig blood were collected and allowed to coagulation. The blood was centrifuged at 4° C., 3,000×g for 15 min. Serum was collected and stored at −80° C.

Serum Antioxidative and Immune Function Measurement

Serum total antioxidative ability, glutathione peroxidase (GPx) activity, superoxide dismutase (SOD) activity, and malondialdehyde (MDA) concentration were detected using relevant kits according to the manufacturer's instruction.

Serum IgG and IgM were measured using turbidimetric inhibition immuno assay.

Serum inflammatory cytokine tumor necrosis factor alpha (TNF-α), interleukin-2 (IL-2) and interleukin-6 (IL-6) were determined using enzme linked immunosorbent assay (ELISA) kit according to manufacturer's instruction.

Statistics

One-way analysis of variance (ANOVA) followed by a lease significant difference (LSD) multiple comparison test was used to determine the statistical significance for multiple comparisons, $P<0.05$ was considered statistically significant. All statistical tests were carried out using SPSS 22 software. All data are presented as the mean±SD.

Results (1) Effect of Biogenic Elemental Selenium Nanostructure on Pig Growth

TABLE 2

Effect of biogenic elemental selenium nanostructure on pig growth

| Item | Control | Experimental group 1 | Experimental group 2 |
|---|---|---|---|
| Initial weight (kg) | 8.08 ± 0.06 | 8.12 ± 0.10 | 8.13 ± 0.10 |
| Final weight (kg) | 23.75 ± 0.49$^a$ | 24.17 ± 0.76$^a$ | 25.72 ± 0.83$^b$ |
| Average daily feed intake (g) | 668.36 ± 18.37 | 654.17 ± 37.64 | 679.23 ± 49.77 |
| Average daily gain (g) | 401.71 ± 11.56$^a$ | 411.54 ± 20.63$^a$ | 451.03 ± 23.97$^b$ |
| Feed/gain ratio | 1.67 ± 0.03$^a$ | 1.59 ± 0.01$^b$ | 1.50 ± 0.03$^c$ |

As shown in Table 2, even though there was no significant difference in average daily feed intake, pigs fed with biogenic elemental selenium nanostructure (experimental group 2) had significant increase of the average daily gain, and decreased feed/gain ratio. The effect of promoting growth by biogenic elemental selenium nanostructure was better than by sodium selenite (experimental group 1).

(2) Effect of BNS on Pig Antioxidative Function

TABLE 3

Effect of biogenic elemental selenium nanostructure on pig antioxidative function

| Item | Control | Experiment group 1 | Experiment group 2 |
|---|---|---|---|
| T-AOC (U/mL) | 2.26 ± 0.11$^a$ | 2.51 ± 0.16$^a$ | 2.93 ± 0.14$^b$ |
| GPx (U/mL) | 219.00 ± 11.72$^a$ | 238.56 ± 13.07$^a$ | 275.05 ± 15.54$^b$ |
| SOD (U/mL) | 138.68 ± 4.54$^a$ | 147.94 ± 5.89$^a$ | 164.48 ± 6.00$^b$ |
| MDA (nmol/mL) | 3.53 ± 0.14$^a$ | 3.31 ± 0.10$^a$ | 2.73 ± 0.10$^b$ |

As shown in Table 3, compared with control group and experimental group 1, biogenic elemental selenium nanostructure significantly increased the activity of T-AOC, GPx and SOD, and decreased MDA concentration in experimental group 2. No significant difference of the parameters was shown comparing experimental group 1 with the control group.

(3) Effect of Biogenic Elemental Selenium Nanostructure on Pig Immune Cytokines Expression

TABLE 4

Effect of BNS on pig immune cytokines expression

| Item | Control | Experimental group 1 | Experimental group 2 |
|---|---|---|---|
| IgG (g/L) | 2.39 ± 0.09$^a$ | 2.66 ± 0.23$^{ab}$ | 3.68 ± 0.35$^c$ |
| IgM (g/L) | 0.66 ± 0.07$^a$ | 0.71 ± 0.07$^a$ | 1.03 ± 0.12$^b$ |
| TNF-α (ng/L) | 33.66 ± 5.17$^a$ | 41.86 ± 4.50$^{ab}$ | 56.01 ± 4.20$^c$ |
| IL-2 (ng/L) | 88.24 ± 7.98$^a$ | 108.19 ± 10.26$^{ab}$ | 131.38 ± 11.80$^b$ |
| IL-6 (ng/L) | 479.44 ± 26.84$^a$ | 571.10 ± 38.62$^{ab}$ | 707.25 ± 52.95$^c$ |

As shown in Table 4, comparing with the control group, Na$_2$SeO$_3$ and biogenic elemental selenium nanostructure significantly elevated serum levels of IgG, IgM, TNF-α, IL-2 and IL-6. The elevated effects on all the serum levels of the biogenic elemental selenium nanostructure group reached to significant levels.

Conclusions

Dietary supplementation with biogenic elemental selenium nanostructure could significantly promote pig growth, decrease feed/gain ratio; and increase the levels of antioxidative activity and immune cytokines. All of the effects were more effective than those of sodium selenite.

What is claimed is:

1. A method of synthesizing biogenic elemental selenium nanoparticles using selenite as starting materials and *Enterobacter. cloacae* Z0206, which is deposited in China General Microbiological Culture Collection Center (CGMCC) on Dec. 3, 2007 with a CGMCC depository No. 2279, as fermentative bacteria, comprising the steps of:

inoculating activated *Enterobacter. cloacae* Z0206 cells to a fermentation broth containing potassium phosphate, and adding sodium selenite solution to obtain an inoculated broth, wherein the final concentration of sodium selenite in the fermentation broth is 10 mM;

shaking and incubating the inoculated broth to obtain a fermented broth, wherein the temperature, rotation speed and incubation time during shaking and incubating step are 32° C., 250 rpm and 144 hours, respectively; and collecting the fermented broth, performing a first centrifugation on the fermented broth to obtain a supernatant, performing a second centrifugation on the supernatant to obtain a sediment, re-suspending the sediment with double distilled water to obtain a suspension, ultrasonicating the suspension, adding hexane to the suspension, and mixing and stratifying the suspension by standing to result in a lower red aqueous phase, wherein the biogenic elemental selenium nanostructures should present in the lower red aqueous phase, wherein parameters of the first centrifugation are 4° C., 5,000×g, 15 minutes, parameters of the second centrifugation are 4° C., 25,000×g, 15 minutes, parameters of the ultrasonication are 25 W, 5 seconds on and 5 seconds off for 15 minutes, and the volume of the hexane is half of the volume of the suspension.

2. The method of claim 1, wherein the fermentation broth consists of sucrose (25 g·L$^{-1}$), yeast extraction (5 g·L$^{-1}$), tryptone (5 g·L$^{-1}$), K$_2$HPO$_4$·3H$_2$O (2.62 g·L$^{-1}$), KH$_2$PO$_4$ (1 g·L$^{-1}$) and MgSO$_4$ (0.5 g·L$^{-1}$), with an initial pH value of 7.5.

* * * * *